United States Patent [19]
McLaughlin

[11] Patent Number: 6,108,850
[45] Date of Patent: Aug. 29, 2000

[54] ACCELERATED METHOD AND INSTRUMENTATION FOR WHITENING TEETH

[76] Inventor: Gerald McLaughlin, 12 Cottonwood Ave., Port Jefferson Station, N.Y. 11776

[21] Appl. No.: 09/045,489

[22] Filed: Mar. 20, 1998

Related U.S. Application Data

[60] Provisional application No. 60/048,423, Jun. 3, 1997.

[51] Int. Cl.[7] ........................................ A46B 11/04
[52] U.S. Cl. ......................... 15/167.1; 132/308; 401/268
[58] Field of Search ................. 424/49, 50, 51, 424/52, 53; 15/167.1; 132/308, 311; 401/268, 282

[56] References Cited

U.S. PATENT DOCUMENTS

| | | | |
|---|---|---|---|
| 4,181,712 | 1/1980 | Rialdi | 424/49 |
| 4,693,622 | 9/1987 | Booth | 401/191 |
| 4,990,089 | 2/1991 | Munro | 433/215 |
| 5,032,178 | 7/1991 | Cornell | 106/35 |
| 5,066,155 | 11/1991 | English et al. | 401/175 |
| 5,264,205 | 11/1993 | Kelly | 424/53 |
| 5,302,374 | 4/1994 | Wagner | 424/52 |
| 5,356,849 | 10/1994 | Matviya et al. | 502/180 |
| 5,403,105 | 4/1995 | Jameson | 401/45 |
| 5,403,578 | 4/1995 | Gordon | 424/53 |
| 5,437,858 | 8/1995 | Hungerbach et al. | 424/53 |
| 5,575,654 | 11/1996 | Fontenot | 433/215 |
| 5,645,428 | 7/1997 | Yarborough | 433/215 |
| 5,648,064 | 7/1997 | Gaffar et al. | 424/53 |
| 5,737,792 | 4/1998 | Quigless | 15/167.1 |

FOREIGN PATENT DOCUMENTS

| | | |
|---|---|---|
| WO97/11676 | 4/1997 | WIPO . |
| WO97/21419 | 6/1997 | WIPO . |

*Primary Examiner*—Robert H. Harrison
*Attorney, Agent, or Firm*—Klarquist Sparkman Campbell Leigh & Whinston, LLP

[57] ABSTRACT

The invention provides a composition whitening teeth, using a bleaching compound and a catalytic activator, where the catalytic activator catalyzes the reaction of a significant portion of the bleaching compound within in a short period of time. A method for whitening teeth by providing a bleaching compound, providing a catalytic agent, and combining the bleaching agent with the catalytic agent so that a reaction of a significant portion of the bleaching agent occurs in a short period of time is also disclosed. A device for whitening teeth, consisting of a toothbrush where at least one of the bristles contains a catalytic activator is also provided. The handle of this device has a reservoir for a bleaching compound and a means for dispensing the bleaching compound. Another device for whitening teeth, consisting of a toothbrush with a catalytic activator capable of catalyzing the reaction of a bleaching compound applied to the head of the device, is further provided.

8 Claims, 1 Drawing Sheet

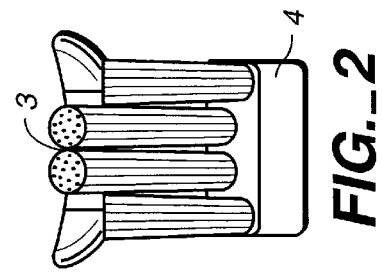
FIG._2
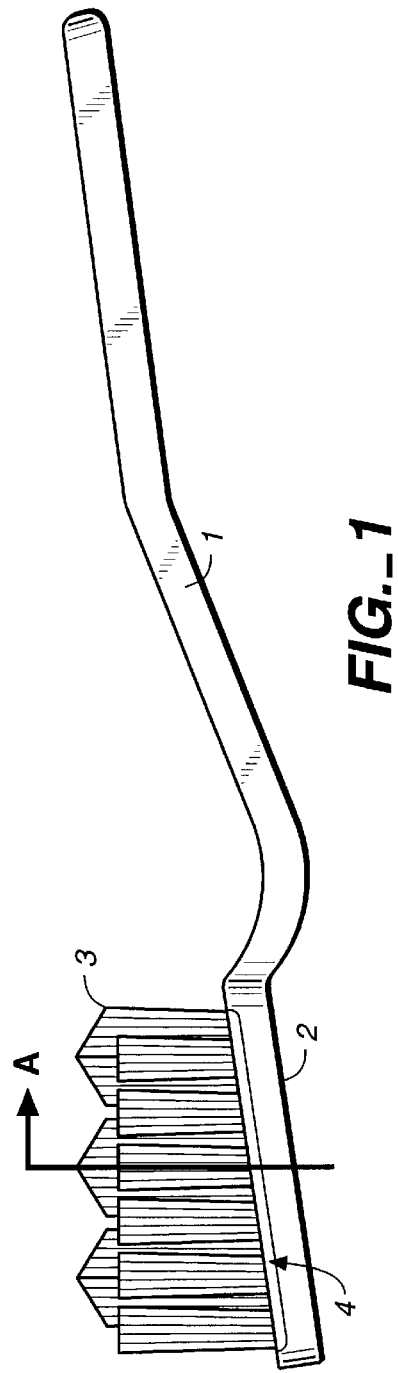
FIG._1
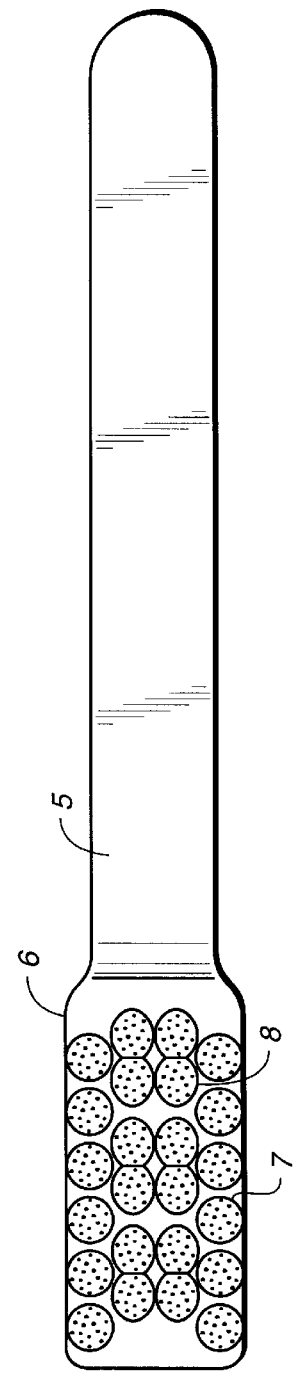
FIG._3

ACCELERATED METHOD AND INSTRUMENTATION FOR WHITENING TEETH

CROSS REFERENCE TO RELATED APPLICATION

This application claims priority from U.S. Provisional Application Serial No. 60/048,423, filed Jun. 3, 1997.

FIELD OF THE INVENTION

The present invention relates to the field of dentistry, and specifically to the whitening of the teeth.

BACKGROUND OF THE INVENTION

Teeth generally become more darkly pigmented with age and exposure to such materials as tea and coffee, and it has long been a goal of dentistry to provide a means to safely and effectively reverse this darkening process. Historically there are two approaches to the problem. The first involves removing pigmentation that has adhered onto the surface of the teeth. This is commonly achieved through the use of abrasives, sometimes augmented with solvents. While rapidly effective, these techniques have the disadvantage of only being able to remove extrinsic stains, leaving all internal pigmentation unchanged. Thus the whitening effect is extremely limited.

A more recent innovation involves a method of using oxidizing agents to penetrate into the tooth structure and bleach out the undesired pigmentation. The active agents are usually either weak solutions of hydrogen peroxide or carbamide peroxide, which is more stable than hydrogen peroxide.

While effective on both extrinsic and intrinsic discolorations, one major problem encountered with this second approach is the enormous amount of treatment time needed to gain adequate penetration of the tooth structure by the whitening agent. At present, the method of application of the whitening agent utilizes either custom or stock trays that are shaped to hold the bleaching agent against the teeth to be whitened. These trays are then filled with the peroxide, and worn for long periods of time, sometimes even overnight. After a series of lengthy treatments, the teeth will usually begin to show the desired whitening effect. The length of these treatments can be discouraging and increases the cost. It is therefore desirable to find a method to more rapidly whiten the teeth.

SUMMARY OF THE INVENTION

In one embodiment, the invention provides a composition whitening teeth, using an effective amount of a bleaching compound and a catalytic activator, where the catalytic activator catalyzes the reaction of a significant portion of the bleaching compound within ten minutes.

In a second embodiment, the invention provides a method for whitening teeth consisting of providing a bleaching compound, providing a catalytic agent, and combining the bleaching agent with the catalytic agent so that a reaction of a significant portion of the bleaching agent occurs within ten minutes.

In another embodiment, the invention provides a device for whitening teeth, consisting of a toothbrush with a head and a handle, where the head has a plurality of bristles, and at least one of the bristles contains a catalytic activator. The handle of this device has a reservoir for a bleaching compound and a means for dispensing the bleaching compound.

In a further embodiment, the invention provides a device for whitening teeth, consisting of a toothbrush with a head and a handle, where the head has an applicator and a catalytic activator capable of catalyzing the reaction of a bleaching compound applied to the head.

BRIEF DESCRIPTION OF THE DRAWINGS

FIG. 1 shows a side view of a toothbrush made in accordance with the present invention that has a compartment for a catalytic activator on the head.

FIG. 2 is a front elevational view thereof.

FIG. 3 shows a cross section of a toothbrush with bristles containing a catalytic activator.

DESCRIPTION OF THE PREFERRED EMBODIMENTS

All publications mentioned herein are incorporated herein by reference for the purpose of describing and disclosing the equipment, compositions, and methodologies which are described in the publications which might be used in connection with the presently described invention.

The invention provides a composition for whitening teeth, consisting of a therapeutically effective amount of a bleaching compound and a catalytic agent, where the catalytic agent is capable of catalyzing the reaction of a significant portion of the bleaching compound within a short period of time. A "bleaching compound" is any compound which has the ability, when activated by a catalyst, of whitening the teeth. Examples of suitable bleaching compounds include an oxygen radical generating agent such as metal ion free peroxides, organic peroxides, and metal ion containing peroxides. Specific, non-limiting examples of bleaching agents suitable for use with the subject invention are carbamide peroxide, carbamyl peroxide, sodium percarbonate, perhydrol urea, and hydrogen peroxide. By "therapeutically effective amount" is meant the quantity of a the bleaching agent, when placed in contact with a catalyst according to the invention, necessary to whiten the teeth of a subject. A subject is any mammal, preferably a human.

Typically the bleaching agent employed in the composition in amounts so that about 3% to 40% by weight comprises the bleaching agent. Preferably, if the bleaching compound is hydrogen peroxide, the concentration of the bleaching compound is from about 3 to 12% by weight. Most preferably, if the bleaching agent is hydrogen peroxide, the concentration of the bleaching compound is from about 6% to about 10% by weight. Preferably, if the bleaching agent is carbamide peroxide, carbamyl peroxide, sodium percarbonate, and perhydrol urea, the concentration of the bleaching compound is from about 10% to about 40% by weight. More preferably, if the bleaching agent is carbamide peroxide, carbamyl peroxide, sodium percarbonate or perhydrol urea, the concentration of the bleaching compound is from about 20% to about 30% by weight.

Assays to determine a therapeutically effective amount of a bleaching compound are known in the art. For example, stained extracted teeth can be used to measure a whitening effect (see Example 1). Other assays, such as an analysis of the effect of a bleaching compound on the soft tissues, may also be used in the determination of a therapeutically effective range of concentrations of a bleaching compound.

The bleaching agent is contained in a vehicle; formulations of vehicles for bleaching agents are well known in the art. The formulation can be aqueous or non-aqueous. As an example, glycerin, and polyethylene glycol in combination with water are useful in formulating the vehicle. Thickening or gelling agents may also be used in the formulation of the bleaching agent. In one example poloxyethylene/polyoxypropylene block copolymers can be utilized. As another example, carbopol polymers can be used. These polymers are well known in the art, and are available commercially.

The composition of the subject invention furtherer consists of a catalytic agent. A "catalytic agent" is a compound or molecule which accelerates the whitening action of the bleaching compound without being consumed in the reaction. In a preferred embodiment, the catalytic agent accelerates the release of oxygen radicals from an oxygen radical generating agent. Examples of such agents include, but are not limited to activated charcoal, platinum, platinum salts, copper, copper salts, palladium, palladium salts, silver, and silver salts. In a preferred embodiment, activated charcoal is used as the catalytic activator. Of particular use with the subject invention is the commercially activated charcoal Centaur, produced by Calgon, Inc. Catalytic agents useful with the subject invention catalyze the reaction of a significant portion of the bleaching compound within a short period of time of coming into contact with the bleaching compound. By "short period of time" is meant in minutes, preferably about ten minutes or less. The catalytic agent may catalyze the reaction of substantially all of the bleaching compound in about ten minutes of coming into contact with the bleaching agent. In one embodiment the catalytic activator catalyzes the reaction of 50% of the bleaching agent, preferably 70% of the bleaching agent, and more preferably 90% of the bleaching agent. Contact of the bleaching compound with the catalytic agent causes the visable evolution of gas within two minutes of contact. "Visable evolution" of a gas, such as oxygen, formed by the contact of the bleaching compound with the catalytic agent can be noted in many ways, such as the formation of bubbles or any sign of gaseous release.

In one embodiment, an abrasive material can be used with the composition of the invention. For example a dicalcium phosphate abrasive may be incorporated into the composition (e.g., see U.S. Pat. No. 5,171,564). Example of dicalcium phosphate abrasives include, but are not limited to dicalcium phosphate dihydrate, anhydrous dicalcium, or calcium pyrophosphate. Other abrasives of use with the subject invention include siliceous materials. Examples of such materials include, but are not limited to, silica abrasives, such as precipitated amorphous hydrated silica, and alumina abrasives, such as alumina trihydrate, aluminum silicate, calcined alumina, and bentonite.

When an abrasive material is included the vehicle may contain water, humectant, surfactant, and a thickener. Examples of humectants are glycerin, sorbitol, and polyethylene glycol (molecular weight 200–1000). Both mixtures of humectants and single humectants can be employed in the composition of the invention. Thickeners may be incorporated in the abrasive component such as natural and synthetic gums such as carrageenan, xantham gum, sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

In another embodiment, an agent for administering fluoride, such as a fluorine providing salt, which has activity against cavities, may be incorporated into the composition of the subject invention. Such materials are characterized by their ability to release fluoride ions in water. Agents for administering fluoride include, but are not limited to, inorganic metal salts such as sodium fluoride, potassium fluoride, and tin fluoride such as stannous fluoride or stannous chlorofluoride, sodium fluorosilicate, ammonium fluorosilicate, and sodium monofluorophosphate.

The composition may also include palliative ingredients for periodontal tissues. Examples of such ingredients include, but are not limited to aloe, eugenol, and vitamin E. Pigments, sweeteners, colors, and flavors may also be incorporated into the composition. The composition may further include an ingredient to decrease tooth sensitivity, such as potassium nitrate. The addition of these components to dental creams, such as toothpaste, are well known in the art.

The invention further provides a method for whitening teeth, by providing a bleaching agent, providing a catalytic agent, and then combining the bleaching agent with the catalytic agent, such that the catalytic agent catalyzes the reaction of a significant portion of the bleaching agent within about ten minutes of combining the bleaching agent with the catalytic agent.

Any convenient means can be utilized for separating the bleaching agent from the catalytic agent prior to the reaction process. In one embodiment, separate containers are used, one of which holds the bleaching agent in liquid form, and one of which holds the catalytic agent in solid or liquid form. The bleaching agent is then mixed with the catalytic agent immediately prior to use. For example, the bleaching agent can be in a liquid form, similar to a mouthwash. The catalytic agent can be in the form of a solid powder, contained in a foil packet. Just prior to use, the catalytic agent is added to the liquid containing the bleaching agent and the liquid is retained in the mouth, similar to a mouthwash, for three to five minutes.

In another embodiment, a single container can be compartmentalized so the bleaching agent is housed separately from the catalytic agent. Upon extrusion form the dual compartment container the bleaching agent is combined with the catalytic agent. For example, the whitening agent and catalytic agents can each be contained in a gel or paste form. Upon extrusion from the container, the two are admixed, and placed on a toothbrush. Brushing for three to five minutes can also result in mixing the catalytic agent with the bleaching agent.

In another embodiment, a stable composition is formed consisting of the catalyst microencapsulated and mixed with the bleaching agent. Techniques for microencapsulation of individual components for tooth and gum dentifrice are well known in the art (see U.S. Pat. No. 5,403,578). The encapsulated material is stable until contacted with water. In this embodiment it is preferable for the base composition of the paste to be free of water. Upon use of the composition, and the addition of water, the bleaching agent is placed in contact with the catalyst.

Either a paste or gel containing the bleaching agent and the catalyst may be prepared. Alternatively, a fabric embedded with the bleaching agent and the catalyst can be produced. Upon the addition of water, thereby wetting the fabric, the bleaching agent and the catalyst are admixed.

In another embodiment, the catalytic agent can be applied on a solid surface, such as a dental tray (e.g., U.S. Pat. No. 4,990,089). The dental tray can be either pre-fabricated or customized. In order to produce a customized dental tray, a sheet of moldable plastic is used that will conform to a mold of an individual's teeth. Production of such trays is well known in the art. In brief: (1) a mold of the teeth to be whitened is prepared, (2) a sheet of plastic material of a appropriate size between 0.01 inch and 0.1 inch thick is obtained, (3) the plastic sheet is placed in a holder, and, if desired, silicone may be sprayed onto the plastic sheet, (4) the plastic sheet is heated until it becomes malleable, (5) the heated sheet is placed over the model, (6) the heated plastic is contoured to the mold, either manually or using a vacuum process, (7) the mold is removed, and (8) the plastic is trimmed. The catalytic agent may be embedded into a sponge which is inserted into the heated plastic. Alternatively, the catalytic agent can be embedded in a fabric which is bonded to the tray after the plastic has cooled. The catalytic agent can also be directly applied or bonded to the surface of the to the cooled plastic, such as by spraying the tray with a solution of copper salts. The bleaching agent is applied to the tray in the form of a paste or a liquid immediately prior to use, and the tray is then applied to the subject's teeth.

In another embodiment, the catalytic agent may be applied to the surface of a toothbrush. A "toothbrush" is a device designed for cleaning teeth that has a region for holding, such as a handle, and a region for cleaning, such as bristles or a sponge. The toothbrush is either manually or mechanically agitated to clean the teeth of a subject. The head of the brush can be made of any appropriate material, such as plastic, and can be designed to contain the catalyst, either by applying the catalytic agent directly to the head of the brush, either on the same side of the brush as the bristles or sponge, or on the opposite side of the brush. The catalytic agent can be embedded in a fabric that is bonded to the head of the brush, or the fabric embedded with the catalytic agent can be inserted into a compartment in the head of the brush.

Referring to FIG. 1 there is shown a toothbrush, comprising a handle (1) and a head (2). The head (2) comprises bristles (3) and a compartment (4) for the insertion of a fabric or gel foam comprising a catalytic agent. The fabric or gel foam comprising the catalytic agent may be removed and replaced with a new piece of fabric or gel foam comprising a catalytic agent when desired.

A front elevational view of the device shown in FIG. 1, where a section is shown looking is the direction of (A), is depicted in FIG. 2. Referring to FIG. 2 it can be seen that the compartment (4) in the head of the brush is open to the upper surface of the brush. The bleaching compound is applied to the bristles prior to use of the toothbrush by the subject; the application of the bleaching compound to the toothbrush results in the catalyst contacting the bleaching compound. The subject then uses the toothbrush to brush the teeth, and the whitening effect is thereby achieved.

Alternatively, the bristles located on the head of the tooth brush can be designed to contain the catalyst: the catalyst can be applied to the surface of the bristle or it can be embedded into one or more of the bristles of the brush. Referring to FIG. 3, there is shown a toothbrush with a handle (5) and a head (6) with bristles (7). One of the of the bristles (8) is embedded with a catalytic agent. It should be noted that any number or conformation of bristles can be embedded with the catalytic agent. The bleaching compound is applied to the bristles prior to use of the toothbrush by the subject; the application of the bleaching compound to the toothbrush results in the catalyst contacting the bleaching compound. The subject then uses the toothbrush to brush the teeth, and the whitening effect is thereby achieved.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLES

Example 1

Stained extracted teeth were sectioned into two equal pieces. Each of the pieces was submerged into a peroxide solution or gel. One piece of each tooth was submerged in peroxide alone, while the other was submerged in hydrogen peroxide with a catalyst, a hydrogen peroxide containing a modifier to raise the pH (either AMP or tris-Amino), or hydrogen peroxide containing both the catalyst and the modifier. Three solutions were tested: (1) 3% hydrogen peroxide, (2) 6% hydrogen peroxide, and (3) 10% hydrogen peroxide. Two gels were tested: (1) a commercially available dentist-supervised bleaching gel containing hydrogen peroxide up to 7%, and (2) a commercially available dentist-supervised bleaching gel containing carbamide peroxide up to 20%. Two catalysts were used in the experiments, either a standard activated charcoal or Centaur (Calgon) activated charcoal. Samples were photographed after three minutes of exposure, and at several other time points.

When a catalyst was used, significant bleaching was noted after twelve minutes. The bleaching was comparable to between 21 and 30 hours of bleaching without the catalytic agent. It was noted that those gels containing large amounts of carbopol provided the least amount of dental bleaching.

Example 2

A catalytic agent was applied to a toothbrush by dipping a wet toothbrush into powdered catalytic agent, or by bonding activated charcoal to a toothbrush head between the bristles. A whitening gel (Natural White) containing 1.5% hydrogen peroxide was applied to the toothbrush and the brush was used to clean a subject's teeth. A whitening effect was noted after one application of three minutes in duration. One subject repeated the application of the whitening gel in the presence of the catalytic agent twice a day for three days. Significant whitening was noted following three days of application.

Example 3

Liquid 3% hydrogen peroxide was mixed with a few drops a mint flavor. A small amount of activated charcoal catalytic agent was placed into a cup, and one-half teaspoon of the peroxide was added. This solution was used to bathe the teeth of subjects for sessions fo three minutes of duration, carried out for twice a day over a period of several days. Visible whitening was noted after two days.

It is to be understood that this invention is not limited to the particular methodology, and that protocols, apparatus, models and reagents described as such may, of course, vary. It is also to be understood that the terminology used herein is for the purpose of describing particular embodiments only, and is not intended to limit the scope of the present invention which will be limited only by the appended claims.

Example 4

A specific formulation of the bleaching compound is as follows:

| Component | Concentration (percent by weight) |
|---|---|
| Hydrogen peroxide | 10% |
| flavoring agent | 1% |
| aloe vera | 2% |
| potassium nitrate | 1% |
| titanium dioxide | 1% |
| sodium lauryl sulfate | 1.5% |
| paste carrier | 83.5% |

In one embodiment, for use with the method of the invention, a catalyst is prepared consisting of activated charcoal and AMP mixed in the ratio of 2:1. The formulation comprising the bleaching compound and the catalyst are combined at the time of use in the ratio of 10:1.

In another embodiment, for use with a device of the invention, the formulation comprising the bleaching compound is placed on the toothbrush with a catalyst embedded into one or more of the bristles of the brush, or with a catalytic agent embedded in a fabric bonded to the head of the brush.

What is claimed is:

1. A device for whitening teeth, said device comprising a toothbrush comprising a head and a handle, said head having a plurality of bristles, wherein at least one bristle comprises a catalytic activator, and said handle comprising a reservoir for a bleaching compound and a means for dispensing said bleaching compound in close proximity to said bristles.

2. The device of claim 1, wherein said bleaching compound is selected from the group consisting of carbamide peroxide, carbamyl peroxide, sodium percarbonate, perhydrol urea, and hydrogen peroxide.

3. The device of claim 1, wherein said catalytic activator is selected from the group consisting of activated charcoal, platinum, a platinum salt, copper, a copper salt, palladium, a palladium salt, silver, and a silver salt.

4. A device for whitening teeth, said device comprising;
a toothbrush comprising a head and a handle, said head comprising an applicator and a catalytic activator capable of catalyzing the reaction of a bleaching compound applied to said head.

5. The device of claim 4, wherein said head further comprises a retaining means for holding a bleaching agent in solid form.

6. The device of claim 4, wherein said applicator is a plurality of bristles.

7. The device of claim 4, wherein said bleaching compound is selected from the group consisting of carbamide peroxide, carbamyl peroxide, sodium percarbonate, perhydrol urea, and hydrogen peroxide.

8. The device of claim 4, wherein said catalytic activator is selected from the group consisting of activated charcoal, platinum, a platinum salt, copper, a copper salt, palladium, a palladium salt, silver, and a silver salt.

* * * * *